(12) United States Patent
Salama

(10) Patent No.: US 10,244,764 B2
(45) Date of Patent: Apr. 2, 2019

(54) GREEN PLANTS TREATED WITH $TIO_2$ TO REMOVE CONTAMINANTS IN AIR

(71) Applicant: Imam Abdulrahman Bin Faisal University, Dammam (SA)

(72) Inventor: Khaled Fikry Salama, Dammam (SA)

(73) Assignee: Imam Abdulrahman Bin Faisal University, Dammam (SA)

( * ) Notice: Subject to any disclaimer, the term of this patent is extended or adjusted under 35 U.S.C. 154(b) by 50 days.

(21) Appl. No.: 15/477,686

(22) Filed: Apr. 3, 2017

(65) Prior Publication Data

US 2018/0279623 A1  Oct. 4, 2018

(51) Int. Cl.
*A01N 3/00* (2006.01)
*A01N 59/16* (2006.01)
*A01H 5/02* (2018.01)

(52) U.S. Cl.
CPC ............... *A01N 59/16* (2013.01); *A01H 5/02* (2013.01); *A01N 3/00* (2013.01); *Y02P 60/247* (2015.11)

(58) Field of Classification Search
CPC ............ A01N 59/16; A01N 3/00; A01H 5/02
USPC ....................................................... 504/187
See application file for complete search history.

(56) References Cited

U.S. PATENT DOCUMENTS

2016/0081281 A1  3/2016  Horinek

FOREIGN PATENT DOCUMENTS

| CN | 103125385 A | 6/2013 |
|---|---|---|
| EP | 1 570 715 A1 | 9/2005 |
| EP | 1 704 769 A1 | 9/2006 |
| WO | WO 2010/098439 A1 | 9/2010 |
| WO | WO 2013/088599 A1 | 6/2013 |

OTHER PUBLICATIONS

Mosaddegh et al. (Phytoremediation of benzene, toluene, ethylbenzene and xylene contaminated air by D. deremensis and O. microdasys plants, Journal of Environmental Health Sci. Eng. 2014; 12:39) (Year: 2014).*

Janine Moll, et al., "Effects of Titanium Dioxide Nanoparticles on Red Clover and Its Rhizobial Symbiont", Plos One, http://journals.plos.org/plosone/article?id=10.1371/journal.pone.0155111,_May 12, 2016, 15 pages.

S. J. B. Al-Maliky, "Control of gaseous pollution via the leaves of non-edible trees", Modern Technologies in Industrial Engineering (MODTECH2015), IOP Conf. Series: Materials Science and Engineering, vol. 95, 2015, 6 pages.

Fan Yang, et al., "Influence of nano-anatase $TiO_2$ on the nitrogen metabolism of growing spinach", Biological Trace Element Research, vol. 110, Issue 2, May 2006, pp. 179-190 (Abstract only).

Yulin Tang, et al., "Synergistic Effects of Nano-Sized Titanium Dioxide and Zinc on the Photosynthetic Capacity and Survival of *Anabaena* sp.", International Journal of Molecular Science, vol. 14, 2013, pp. 14395-14407.

* cited by examiner

Primary Examiner — Johann R Richter
Assistant Examiner — Danielle Sullivan
(74) Attorney, Agent, or Firm — Oblon, McClelland, Maier & Neustadt, L.L.P.

(57) ABSTRACT

A method of reducing contaminants in air, including applying titanium dioxide-containing growth media to at least one of a *Myrtus communis* plant root, stem, and leaf, and growing the plant. The growth media is a liquid growth media, a gel growth media, or both. The plant is then exposed to contaminant-containing air. The contaminant is $CO_2$, $SO_2$, formaldehyde, CO, benzene, toluene, xylene, ethyl benzene, or a combination thereof. The contaminant concentration in the air is reduced relative to a contaminant concentration in the air prior to the exposing. A plant portion having a portion of a *Myrtus communis* plant comprising an infused titanium dioxide is also described. The portion is at least one of a root, stem, or leaf. In a closed environment, the plant portion reduces the concentration of a contaminant in the air in the closed environment.

10 Claims, 2 Drawing Sheets

GREEN PLANTS TREATED WITH TIO₂ TO REMOVE CONTAMINANTS IN AIR

BACKGROUND OF THE INVENTION

Technical Field

The present invention relates to a plant growth method that enhances air quality by reducing contaminants in air, and a titanium oxide-rich plant.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Nanotechnology is one of the most important tools in modern science, yet only a few attempts have been made to apply these advances for increasing the efficiency of green plants for purifying air. The efficiency of green plants for purifying air may be improved by increasing plant growth and chlorophyll content in the plant to aid in removal of toxic air pollutants from indoor environments like chemical and microbiological teaching laboratories and industrial facilities. Titanium oxide ($TiO_2$) is an inorganic material that can function as a photo-catalyst to accelerate the chemical breakdown of toxic air pollutants. *Myrtus communis* L. (Arabic name: Aas or Hadas; common name: myrtle) is an important evergreen leafy plant belonging to the Myrtaceae family. It grows in a variety of climates and in Saudi Arabia. It has been reported that parts of the plant are rich sources of bioactive compounds.

Plants absorb carbon dioxide in air, assimilate the carbon dioxide via photosynthesis, and release oxygen. Some plants have the capability to remove volatile organic compounds (VOCs) from air. Plants that improve air quality are widely used in facilities (e.g., hospitals and schools), offices, and the like. The air quality-improving effect of plants having foliage (i.e., "foliage plants") can be improved by promoting photosynthesis.

The technology for growing crops, flowers, and the like has been widely developed. However, sufficient research and development for improving the function of foliage plants (e.g., potted foliage plants) have not yet been conducted.

In view of the forgoing, an objective of the present invention is to employ a myrtle plant treated with known concentrations of titanium dioxide to reduce toxic air pollutants.

BRIEF SUMMARY OF THE INVENTION

According to a first aspect, the disclosure relates to a method of reducing contaminants in air, including applying titanium dioxide-containing growth media to at least one of a *Myrtus communis* plant root, stem, and leaf, and growing the plant, wherein the growth media is a liquid growth media, a gel growth media, or both; exposing the plant to contaminant-containing air, wherein the contaminant is $CO_2$, $SO_2$, formaldehyde, CO, benzene, toluene, xylene, ethyl benzene, or a combination thereof, wherein a contaminant in the air is reduced by 10% to 98% relative to the concentration of the contaminant in the contaminant-containing air prior to the applying and exposing.

In some implementations, the growth media has a concentration of titanium dioxide in the range of 0.5 ppm to 10 ppm.

In some implementations, the contaminant in the contaminant-containing air is formaldehyde at 0.2 ppm to 0.3 ppm, and a duration of the exposure is 4 hours to 8 hours, which reduces the formaldehyde concentration to 10 ppb to 200 ppb.

In some implementations, the contaminant in the contaminant-containing air is a combination of $CO_2$, $SO_2$, formaldehyde, CO, benzene, toluene, xylene, and ethyl benzene at 300 ppb to 400 ppb, and a duration of the exposure is 4 hours to 8 hours, which reduced the concentration of the contaminant to 10 ppb to 300 ppb.

In some implementations, a contaminant concentration in the contaminant-containing air is in the range of 1 ppb to 100 ppm.

In some implementations, the contaminant in the contaminant-containing air is reduced to a contaminant concentration of 0.25 ppb to 50 ppm.

In some implementations, the plant is exposed to the contaminant-containing air for 24 hours to 96 hours.

In some implementations, the titanium dioxide-containing growth media does not contain potassium silicate.

In some implementations, the titanium dioxide is a nanoparticle.

In some implementations, an average particle size of the nanoparticle is 10 nm to 25 nm.

According to a second aspect, the present disclosure relates to a portion of a *Myrtus communis* plant comprising titanium dioxide (e.g., titanium dioxide infused in the plant), wherein the portion is at least one of a root, stem, or leaf, wherein the portion of the plant in a closed environment reduces the concentration of a contaminant in contaminant-containing air in the closed environment at a rate of 2%-98% greater than a plant without infused titanium dioxide in the closed environment.

In some embodiments, the infused titanium dioxide comprises a titanium dioxide nanoparticle.

In some embodiments, an average particle size of the titanium nanoparticle is 10 nm to 25 nm.

In some embodiments, the portion of the plant reduces a contaminant concentration in the contaminant-containing air at a rate of 0.7 ppb/hour to 50 ppm/hour.

In some embodiments, the infused titanium oxide is collocated with a chlorophyll containing organelle of the portion of the plant.

In some embodiments, the infused titanium dioxide in the plant portion is a density over a chlorophyll containing surface of 2 $TiO_2$ nanoparticles/$\mu m^2$ to 50 nanoparticles/$\mu m^2$.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Figure 1:
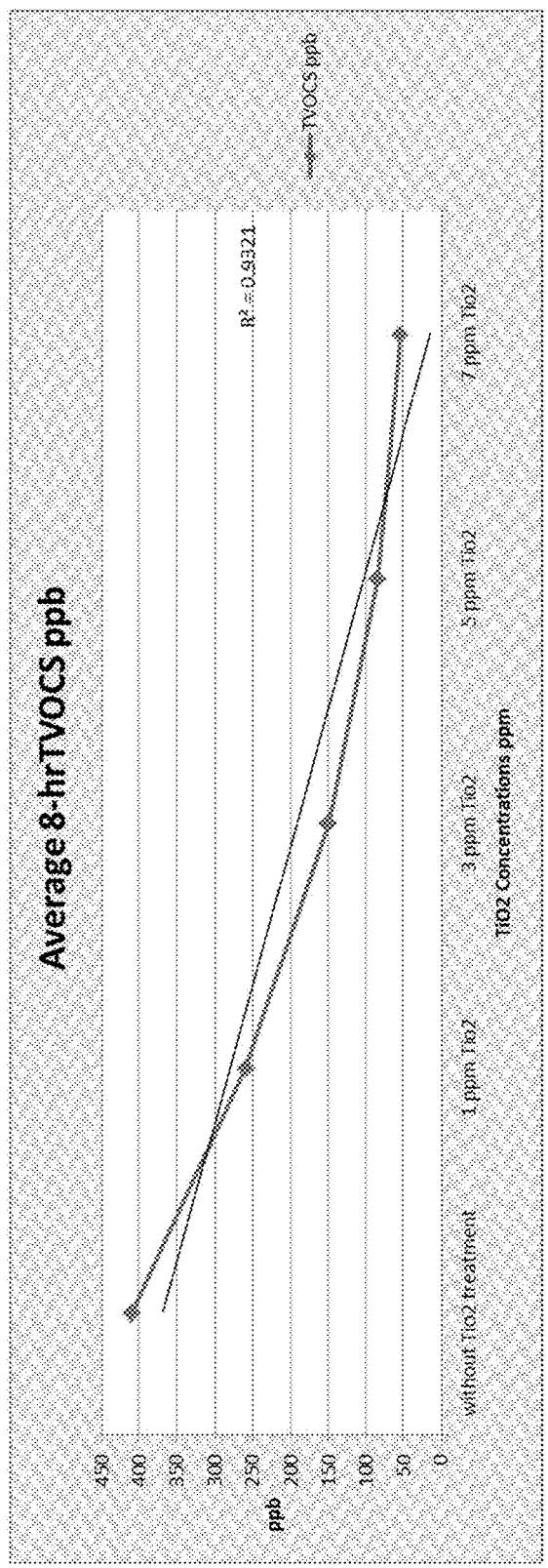
FIG. 1 is a graph of the 8-hour averaged total volatile organic compound concentration being reduced by a plant with an increasing amount of $TiO_2$ sprayed on its stem and leaves.
Figure 2:
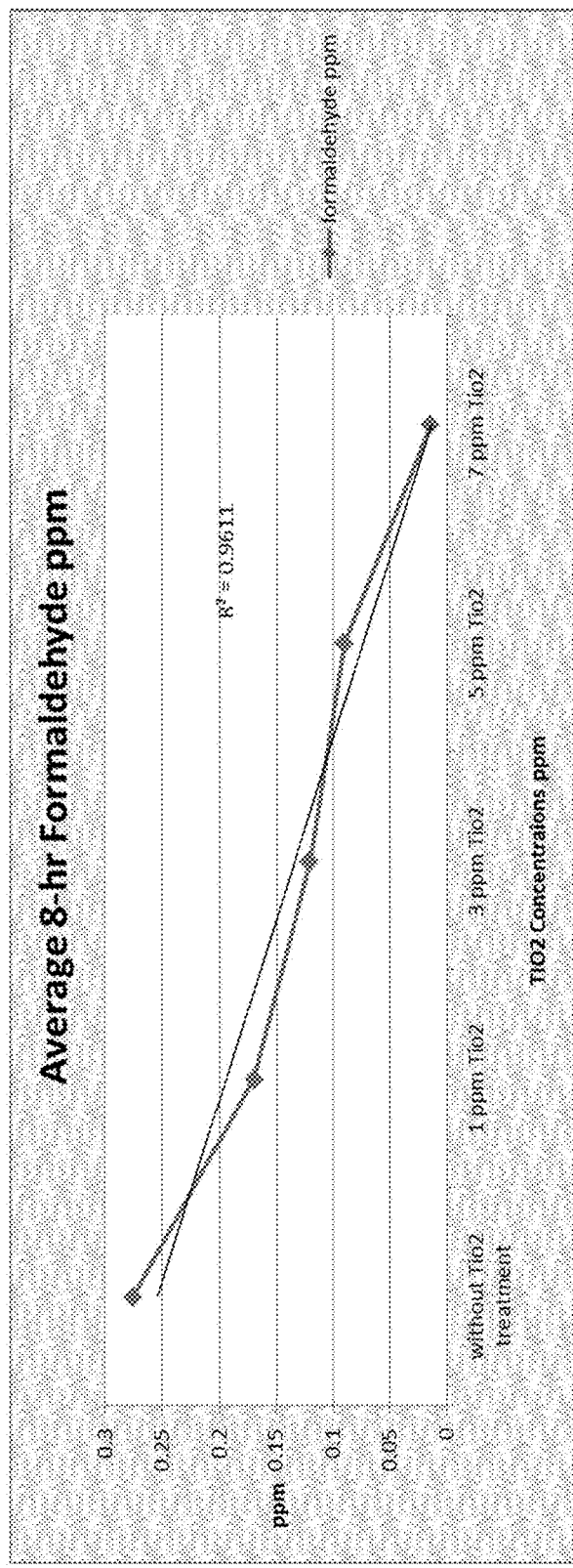
FIG. 2 is a graph of the 8-hour averaged formaldehyde concentration being reduced by a plant with an increasing amount of $TiO_2$ sprayed on its stem and leaves.

Embodiments of the present disclosure will now be described more fully hereinafter with reference to the accompanying drawings, in which some, but not all embodiments of the disclosure are shown.

An aspect of the present disclosure relates to a method of reducing contaminants in air. The method includes applying titanium dioxide-containing growth media to at least one of a *Myrtus communis* plant root, stem, and leaf, growing the plant, and exposing the *Myrtus communis* plant to contaminant-containing air. The contaminant-containing air may include contaminants such as $CO_2$, $SO_2$, formaldehyde, CO, benzene, toluene, xylene, ethyl benzene, or a combination thereof. As a result of the presently disclosed method, the contaminant concentration in the air may be reduced by 10% to 98%, 15% to 90%, 20% to 80%, or 40% to 60% relative to the contaminant concentration of the contaminant in the contaminant-containing air prior to exposing the air to the portion of the titanium dioxide-containing *Myrtus communis* plant.

The growth media described herein may be a liquid growth media, a gel growth media, or both. The gel growth media comprise gelatin, cellulose, chitosan, pectin, agarose, alginate or the like. The liquid growth media and/or the gel growth media may include polyethylene glycol, water, sucrose, vitamins, plant growth hormones such as auxins, and plant growth regulators such as cytokinins, fertilizers, trace minerals and elements, and, optionally, one or more penetrants such as an ionic surfactant, a non-ionic surfactant and/or DMSO. Vitamins may include Vitamin E, Vitamin B, and Vitamin C. Trace minerals and elements may include ions or polyatomic ions, and salts thereof, including, nitrogen, phosphorus, potassium, calcium, sulfur, magnesium, boron, chlorine, manganese, iron, zinc, copper, molybdenum, nickel, cobalt, aluminum, silicon, vanadium, and selenium. In some embodiments, the liquid and/or gel growth media may include 5% to 30%, 10% to 20%, or 15% to 18% urea, relative to the total volume of the growth media. In some embodiments, the liquid and/or gel growth media may include phosphate from 1% to 10% or 5% to 8%, relative to the total volume of the growth media. In some embodiments, phosphate may be in the form of potassium phosphate or ammonium phosphate. In some embodiments, the liquid and/or gel growth media may include potassium in the form of potash at 1% to 20%, 5% to 15%, or 10% to 12% relative to the total volume of the growth media. In one embodiment, the liquid and/or gel growth media explicitly exclude potassium silicate, silicon carbide, silicon dioxide, and/or aluminum oxide. The growth media may be 75% to 95%, or 85% to 90% water and 2% to 15%, 3% to 10%, or 5% to 8% polyethylene glycol. Sucrose, vitamins, plant growth hormones, and plant growth regulators in the growth media may comprise 0.5% to 5%, 1% to 4%, or 2% to 3% by weight relative to the total weight of the growth media. In some implementations, the growth media may have a concentration of the titanium dioxide in the range of 0.5 ppm to 10 ppm, 1 ppm to 9 ppm, 3 ppm to 6 ppm, or 4 ppm to 5 ppm.

Applying the growth media to the *Myrtus communis* plant may include spraying, painting, or misting the leaves and stems of the plant, pouring the growth media into a container of the plant, and/or bottom-watering of a plant container. Spraying the growth media onto a leaf and/or stem of the plant may increase the plant's rate of photosynthesis by increasing the amount of radiation absorbed by the plant. Bottom-watering is a method of contacting soil and roots of the plant first with the liquid and/or gel growth media. The liquid and/or gel growth media may preferably be applied to the vicinity of the root hairs of the plant using a bottom-watering method. The growth media may be mixed into soil of a potted *M. communis* plant or mixed into a hydroponics system sustaining a *M. communis* plant. The growth media may access 2% to 100%, 5% to 90%, 15% to 80%, 20% to 70%, 20% to 60%, or 30% to 50% of the roots of the *M. communis* plant grown in soil or in a hydroponic system. During the growth of the plant over a duration of 1 hour to 10 hours, the plant may absorb the $TiO_2$ through the roots of the plant resulting in a distribution of the $TiO_2$ throughout the plant, with at least 2% of the total absorbed $TiO_2$ in the leaves, at least 10% in the leaves, at least 20% in the leaves, at least 40% in the leaves, or at least 50% in the leaves. The absorption of the $TiO_2$ through the plant roots may increase the plant's rate of photosynthesis. Furthermore, the absorption by the plant roots may affect the plant's nitrogen metabolism, helping the plant to absorb nitrate and form protein and chlorophyll from inorganic nitrogen. This effect on nitrogen metabolism may be dependent on the soil composition and other soil nutrients. Either application method of the growth media, whether to the stem and leaves or to roots, may also increase stem elongation and/or water absorption.

Growth of the *Myrtus communis* plant may be observed physically and/or chemically. Physical growth includes changes in the plant's physiology including height and mass. Growth also includes the production of fruits and flowers as well as foliage. Growth does not require an increase in mass of the plant. Growing the *Myrtus communis* plant also includes absorbing or adsorbing the $TiO_2$ into the vascular system of the plant. In one embodiment the physical features of the plant do not change after growth with the growth media, but $TiO_2$ is present by transportation and/or transpiration of the plant.

$TiO_2$ is a metal oxide which may increase a rate of oxidation of contaminants in air upon interacting with a chlorophyll containing surface of a *Myrtus communis* plant. $TiO_2$ may increase the rate of oxidation of contaminants by 2% to 90%, 5% to 75%, 15% to 50%, 20% to 40%, or 25% to 35% relative to an untreated plant. The $TiO_2$ may provide a free electron upon photo-oxidation under sunlight or UV light. The free electron may then generate hydroxyl radicals and/or oxygen radicals which may form hydrogen peroxide in a cascade of reactions eventually resulting in the degradation of contaminants. In the present method, the *Myrtus communis* plant having $TiO_2$ in the growth media may in some implementations absorb the $TiO_2$ into the plant. The $TiO_2$ may coat the chlorophyll containing surfaces of the plant. The $TiO_2$ may be distributed on 5% to 75%, 10% to 50%, or 20% to 30% of the surfaces of the plant. The $TiO_2$ may oxidize and degrade the contaminants in the contaminant-containing air surrounding the plant. In some implementations the $TiO_2$ is absorbed and/or transported by the vasculature in the plant via the roots of the plant, and may contribute to the degradation of contaminants absorbed into the chlorophyll containing surface of the plant. In some implementations, the $TiO_2$ may contribute to photocatalytic reduction of contaminants, enhancement of plant growth, and enhancement of photosynthesis. $TiO_2$ may prolong the photosynthesis mechanism by transforming light energy to active electrons and increasing chemical activity in chloroplasts (i.e., chlorophyll containing organelles of plants). In some implementations, the titanium dioxide is in the form of nanoparticles having an average particle size of 10 nm to 25 nm, 12 nm to 22 nm, 15 nm to 20 nm, or 17 nm to 18 nm.

In one embodiment of the invention the $TiO_2$ particles are functionalized with one or more organic or inorganic groups covalently or ionically bonded to the $TiO_2$ particles. Covalently bonded materials may include compounds that are able to form covalent bonds with the surface of the titanium dioxide particles. Especially useful in this regard are epoxy-functionalized materials and materials having alkoxy silane functional groups of formula, for example, $R^1Si(OR^2)_3$, where $R^1$ and $R^2$ are hydrocarbon groups and/or heteroatom-containing hydrocarbon groups. It is particularly preferable that one or more covalently-bonded materials is ionic and/or hydrophilic in nature to permit better suspension, dissolution, or mobility of the titanium dioxide particles in aqueous media applied to or absorbed by the plant.

Titanium dioxide particles having surfaces modified with one or more peptides and/or biologically compatible materials are especially preferred. The biologically compatible materials may be directly, covalently, or ionically bonded to the surface of the $TiO_2$ particles or may be bonded to the surface of the titanium dioxide particles through one or more linker units. A linker unit may include, for example, an alkoxy silane component that permits strong covalent bonding to the surface of the $TiO_2$ particle. Peptides such as amino acid sequences including, for example, repeating glycine units, are especially preferred. In another embodiment of the invention the peptides are covalently bonded directly to the surface of the $TiO_2$ particle which has been modified by one or more physical or chemical techniques to induce ionic character onto a surface of the $TiO_2$ nanoparticles. Other amino acids that may be advantageously bonded to the surface of the titanium particles include alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine. Acid group-containing amino acids are especially preferred for cross compatibility between aqueous media and the vascular system of the plant.

The exposing may include placing the plant having the $TiO_2$ in the growth media into a closed space, such as an indoor office, laboratory, work room, closet, or other enclosed space having limited air circulation. The air circulation of an enclosed space may be less than 1500 cfm, less than 1250 cfm, less than 1000 cfm, less than 750 cfm, less than 500 cfm, less than 250 cfm, or less than 100 cfm and preferably greater than 1 cfm, more preferably greater than 10 cfm. The exposing may be for a duration of 1 hour to 336 hours, 3 hours to 312 hours, 6 hours to 288 hours, 12 hours to 264 hours, 36 hours to 240 hours, 72 hours to 216 hours, 96 hours to 192 hours, 120 hours to 168 hours, or 122 hours to 144 hours. In another embodiment, the plant treated with the titanium dioxide-containing growth media can be exposed to the contaminant-containing air on a continuous or substantially continuous basis throughout the lifespan of the plant. The exposing may occur in a room having lighting. The lighting may have wavelengths of 500 nm to 1000 nm, 550 nm to 800 nm, or 600 nm to 750 nm. The lighting may include, but is not limited to light emitting diodes (LED), fluorescent lights, halogen lights, metal halide lights, incandescent lights, and sodium lighting. The plant may be exposed to the lighting under 5 watts/sq. ft. to 60 watts/sq. ft., 10 watts/sq. ft. to 50 watts/sq. ft., or 25 watts/sq. ft. to 35 watts/sq. ft. In some implementations, the plant may be exposed to sunlight as a light source within the closed space.

In some implementations, the contaminants may be absorbed through a respiratory, transpiration, and/or adsorption action of the plant with the surrounding contaminant-containing air. A rate at which the contaminants may be absorbed from the contaminant-containing air by the plant may be 0.5 mg/mL/hour to 50 mg/mL/hour, 1 mg/mL/hour to 40 mg/mL/hour, 5 mg/mL/hour to 30 mg/mL/hour, or 10 mg/mL/hour to 20 mg/mL/hour.

In some implementations, the contaminant concentration in the contaminant-containing air is in the range of 1 ppb to 100 ppm, 2 ppb to 90 ppm, 10 ppb to 80 ppm, 20 ppb to 70 ppm, 40 ppb to 60 ppm, 80 ppb to 40 ppm, 100 ppb to 20 ppm, 250 ppb to 1 ppm, or 500 ppb to 750 ppb. In some implementations, the contaminant concentration in the contaminant-containing air is reduced to 0.25 ppb to 50 ppm, 0.5 ppb to 40 ppm, 1 ppb to 30 ppm, 5 ppb to 20 ppm, 10 ppb to 10 ppm, 25 ppb to 1 ppm, 50 ppb to 900 ppb, 100 ppb to 800 ppb, 200 ppb to 750 ppb, or 500 ppb to 550 ppm after the exposing. In some implementations, the plant is exposed to the contaminant-containing air for 24 hours to 96 hours, 36 hours to 72 hours, or 48 hours to 60 hours.

In some implementations, the contaminant in the contaminant-containing air is formaldehyde at a formaldehyde concentration of 0.2 ppm to 0.3 ppm, or 0.25 to 0.275 ppm, and is reduced to 10 ppb to 200 ppb, 50 ppb to 150 ppb, 75 ppb to 125 ppb, or 90 ppb to 100 ppb after the exposing for a duration of 4 hours to 8 hours, or 6 to 7 hours.

In some implementations, the contaminant in the contaminant-containing air is a combination of $CO_2$, $SO_2$, formaldehyde, CO, benzene, toluene, xylene, and ethyl benzene having a combined contaminant concentration of 300 ppb to 400 ppb, or 325 ppb to 375 ppb that is reduced to 10 ppb to 300 ppb, 50 ppb to 250 ppb, 75 ppb to 225 ppb, 100 ppb to 200 ppb, or 125 ppb to 175 ppb after the exposing for a duration of 4 hours to 8 hours, or 6 to 7 hours. In the combination of $CO_2$, $SO_2$, formaldehyde, CO, benzene, toluene, xylene, and ethyl benzene, $CO_2$ may be present at a concentration of 10 ppb to 150 ppb, 50 ppb to 125 ppb, or 75 ppb to 100 ppb; CO may be present at a concentration of 10 ppb to 150 ppb, 50 ppb to 125 ppb, or 75 ppb to 100 ppb; $SO_2$ may be present at a concentration of 1 ppb to 15 ppb, or 5 ppb to 10 ppb; and formaldehyde, benzene, toluene, xylene, ethyl benzene may have a total concentration of 5 ppb to 100 ppb, 10 ppb to 80 ppb, 25 ppb to 75 ppb, or 40 ppb to 50 ppb.

In another embodiment of the invention the portion of the plant that has been contacted with the $TiO_2$-containing growth media is dried prior to contact with a contaminant-containing atmosphere. The plant portion may contain $TiO_2$ absorbed onto a surface of dried leaf, stem, or root material, or, alternatively or in addition, may contain $TiO_2$ particles dispersed throughout the plant material in a homogeneous fashion or collected in particular portions of the plant which ordinarily contain a higher concentration of organelles. The plant portion in its dry form may contain water in an amount of up to 10% by weight based on the total weight of the dried plant portion, preferably no more than 5%, and most preferably no more than 1% water. Regardless of whether the titanium dioxide is present within the cellular structure of the dried plant or absorbed onto its surface, the plant portion may be contacted with the contaminant-containing atmosphere to reduce contaminants such as those described herein above. Utilization of the $TiO_2$-containing dried plant portion substantially increases the capability of the dried plant material to reduce contaminants in comparison to dried plant material that has not been treated with a $TiO_2$-containing growth media. Preferably the $TiO_2$-containing dried plant material is able to reduce contaminants with an efficiency of more than 5%, more than 10%, more than 20%, more than 30%, more than 50%, or more than 100% in comparison to dry plant material made from a plant which has not been contacted with a $TiO_2$-containing growth media. Efficiency of contaminant removal is measured based on the molar concentration of contaminants present in the contaminant-containing air prior to and after contact with the $TiO_2$-containing dried plant material.

According to a second aspect, the present disclosure relates to a plant portion of a *Myrtus communis* plant comprising an infused titanium dioxide. The titanium dioxide may include the titanium dioxide nanoparticles as described herein. The portion is at least one of a root, stem, flower, fruit, seed, legume, or leaf. The plant portion may have a capability to regenerate from a cutting. A cutting is a piece of a plant that is used in horticulture for vegetative (asexual) propagation. The piece of the plant is placed in a suitable medium such as moist soil. If the conditions are suitable, the plant piece will begin to grow as a new plant independent of the parent, a process known as striking. A stem cutting produces new roots, and a root cutting produces new stems. Some plants can be grown from leaf pieces, called leaf cuttings, which produce both stems and roots.

The portion of the plant may be placed in the closed environment, as described herein, to reduce the concentration of a contaminant in contaminant-containing air in the closed environment at a rate of 2% to 98%, 5% to 95%, 10% to 90%, 20% to 80%, 30% to 70%, or 40% to 60% greater than a plant portion without infused titanium dioxide in the closed environment. In some embodiments, before the portion of the plant is in the closed environment, a contaminant concentration in the contaminant-containing air is in the range of 1 ppb to 100 ppm, 2 ppb to 90 ppm, 10 ppb to 80 ppm, 20 ppb to 70 ppm, 40 ppb to 60 ppm, 80 ppb to 40 ppm, 100 ppb to 20 ppm, 250 ppb to 1 ppm, or 500 ppb to 750 ppb. In some embodiments, after the portion of the plant is in the closed environment for at least 1 hour, at least 30 minutes, at least 20 minutes, or at least 10 minutes, the contaminant concentration in the contaminant-containing air is in the range of 0.25 ppb to 50 ppm, 1 ppb to 40 ppm, 100 ppb to 30 ppm, 500 ppb to 20 ppm, 750 ppb to 10 ppm, or 1 ppm to 5 ppm. In some embodiments, the portion of the plant reduces a contaminant concentration in the contaminant-containing air at a rate of 0.7 ppb/hour to 50 ppm/hour, 1 ppb/hour to 40 ppm/hour, 10 ppb/hour to 30 ppm/hour, 25 ppb/hour to 20 ppm/hour, 50 ppb/hour to 10 ppm/hour, 75 ppb/hour to 1 ppm/hour, 100 ppb/hour to 900 ppb/hour, 300 ppb/hour to 700 ppb/hour, or 500 ppb/hour to 550 ppb/hour.

The portion of the plant may be infused with the titanium dioxide by applying the liquid and/or gel growth media having titanium dioxide as described herein. The portion of the plant may have obtained the infused $TiO_2$ as part of a growing plant or after cutting. In some implementations, the infused $TiO_2$ may be absorbed by the portion of the plant by the liquid growth media sprayed onto the chlorophyll containing surface of the plant.

In some embodiments, the infused titanium dioxide may have a density over the chlorophyll containing surface of 2 $TiO_2$ nanoparticles/$\mu m^2$ to 50 nanoparticles/$\mu m^2$, 5 $TiO_2$ nanoparticles/$\mu m^2$ to 40 nanoparticles/$\mu m^2$, 10 $TiO_2$ nanoparticles/$\mu m^2$ to 30 nanoparticles/$\mu m^2$, or 20 $TiO_2$ nanoparticles/$\mu m^2$ to 25 nanoparticles/$\mu m^2$. In some implementations, the infused $TiO_2$ may circulate through a plant portion's vasculature. In some embodiments, the infused titanium oxide is collocated with the chlorophyll containing organelles of the portion of the plant. "Collocated with the chlorophyll containing organelles" may be defined as the titanium oxide nanoparticles being located inside a chloroplast or within 100 nm, within 90 nm, within 80 nm, within 70 nm, within 60 nm, or within 50 nm of a chloroplast.

The examples below are intended to further illustrate a plant growth method that enhances an air quality-improving effect by promoting photosynthesis, photo-oxidation of contaminants in air, and a titanium oxide-rich plant and are not intended to limit the scope of the claims.

Example

The following data were recorded in laboratories. The experiment was conducted over five working days in selected laboratories where daily data were recorded without the use of $TiO_2$ nanoparticles, and for others, $TiO_2$ nanoparticles were applied in different concentrations with similar experimental settings. Over 8-hour periods, multi-readings were recorded at each hour of the day and the 8-hour averages were calculated. These averages are shown in Table 1. The 8-hour average levels of total volatile organic compounds (TVOCs) in a first lab are also represented in FIG. 1, and the 8-hour average levels of formaldehyde in a second lab are also represented in FIG. 2. The data were recorded for the *Myrtus communis* L. plant (Arabic name: Aas or Hadas) treated by different concentrations of $TiO_2$ nanoparticles having an average particle size of 15 to 20 nm. The preliminary data revealed a significant decline in the levels of both TVOCs and formaldehyde with the gradual increase in the concentration of $TiO_2$ nanoparticles sprayed directly onto the exposed stem and leaves. The data were collected under controlled levels of humidity, temperature, and air flow exchange. However, other toxic air pollutants such as CO, $NO_2SO_2$, benzene, toluene, and xylene were tested and indicated a different removal efficiency when recorded under similar settings.

TABLE 1

| Day | $TiO_2$ treatment | TVOCs (avg ppb) | Formaldehyde (avg ppm) | Relative Humidity (%) | T (° C.) | Air Velocity (m/s) | Air Change per hour (ACH) |
|---|---|---|---|---|---|---|---|
| 1 | none | 410 | 0.275 | 56 | 22.1 | 0.07 | 11 |
| 2 | 1 ppm | 260 | 0.17 | 57 | 22.8 | 0.08 | 10 |
| 3 | 3 ppm | 150 | 0.12 | 55 | 21.7 | 0.08 | 12 |
| 4 | 5 ppm | 85 | 0.09 | 60 | 20.2 | 0.09 | 11 |
| 5 | 7 ppm | 54 | 0.014 | 62 | 22.4 | 0.09 | 12 |

The invention claimed is:

1. A method of reducing contaminants in air, comprising:

applying a titanium dioxide-containing growth media to at least one of a root, stem, and leaf of a *Myrtus communis* plant, and growing the *Myrtus communis* plant, wherein the growth media is a liquid growth media, a gel growth media, or both to form a titanium dioxide-containing *Myrtus communis* plant;

exposing the titanium dioxide-containing *Myrtus communis* plant to contaminant-containing air comprising at least one contaminant selected from the group consisting of $CO_2$, $SO_2$, formaldehyde, CO, benzene, toluene, xylene, and ethyl benzene, wherein a contaminant concentration in the contaminant-containing air is reduced by 10% to 98% relative to a contaminant concentration in the contaminant-containing air prior to the exposing.

2. The method of claim 1, wherein the titanium dioxide-containing growth media has a titanium dioxide concentration in the range of 0.5 ppm to 10 ppm.

3. The method of claim 2, wherein the contaminant in the contaminant-containing air is formaldehyde, and a formaldehyde concentration of 0.2 ppm to 0.3 ppm is reduced to 10 ppb to 200 ppb after the exposing for a duration of 4 hours to 8 hours.

4. The method of claim 2, wherein the contaminant in the contaminant-containing air is a combination of $CO_2$, $SO_2$, formaldehyde, CO, benzene, toluene, xylene, and ethyl benzene having a combined contaminant concentration of 300 ppb to 400 ppb that is reduced to 10 ppb to 290 ppb after the exposing for a duration of 4 hours to 8 hours.

5. The method of claim 1, wherein the contaminant concentration in the contaminant-containing air is in the range of 1 ppb to 100 ppm prior to the exposing.

6. The method of claim 1, wherein the contaminant concentration in the contaminant-containing air is 0.25 ppb to 50 ppm after the exposing.

7. The method of claim 1, wherein the titanium dioxide-containing *Myrtus communis* plant is exposed to the contaminant-containing air for 24 hours to 96 hours.

8. The method of claim 1, wherein the titanium dioxide-containing growth media does not contain potassium silicate.

9. The method of claim 1, wherein the titanium dioxide is a nanoparticle.

10. The method of claim 9, wherein an average particle size of the nanoparticle is 10 nm to 25 nm.

* * * * *